United States Patent [19]

Tanabe et al.

[11] 4,093,633

[45] June 6, 1978

[54] PROCESS FOR PREPARING TETRAHYDROFURAN

[75] Inventors: Yasuo Tanabe; Jun Toriya; Masato Sato; Ken Shiraga, all of Kurashiki, Japan

[73] Assignee: Mitsubishi Chemical Industries Limited, Tokyo, Japan

[21] Appl. No.: 763,506

[22] Filed: Jan. 28, 1977

[30] Foreign Application Priority Data

Feb. 4, 1976  Japan .................................. 51-11078

[51] Int. Cl.$^2$ ........................................... C07D 307/08
[52] U.S. Cl. ................................................. 260/346.11
[58] Field of Search ...................... 260/346.11, 346.1 R

[56] References Cited

U.S. PATENT DOCUMENTS

| 2,544,899 | 3/1951 | Reynolds et al. ..................... 260/333 |
| 3,694,465 | 9/1972 | Kisaki et al. ................... 260/346.1 R |
| 3,726,905 | 4/1973 | Coate et al. .................... 260/346.1 R |

FOREIGN PATENT DOCUMENTS

| 546,591 | 9/1957 | Canada ........................... 260/346.1 R |
| 1,170,222 | 11/1969 | United Kingdom .......... 260/346.1 R |
| 174,636 | 11/1965 | U.S.S.R. ......................... 260/346.1 R |

*Primary Examiner*—Richard L. Raymond
*Attorney, Agent, or Firm*—Bierman & Bierman

[57] ABSTRACT

In the process for preparing tetrahydrofuran by the dehydrocyclization of 1,4-butanediol in the presence of a non-volatile acid catalyst, wherein vapor mixture of water and tetrahydrofuran is continuously taken out from the reaction zone and subjected to the azeotropic distillation in three distillation columns operated under specified conditions thereby obtaining tetrahydrofuran of high quality in a high yield.

10 Claims, 1 Drawing Figure

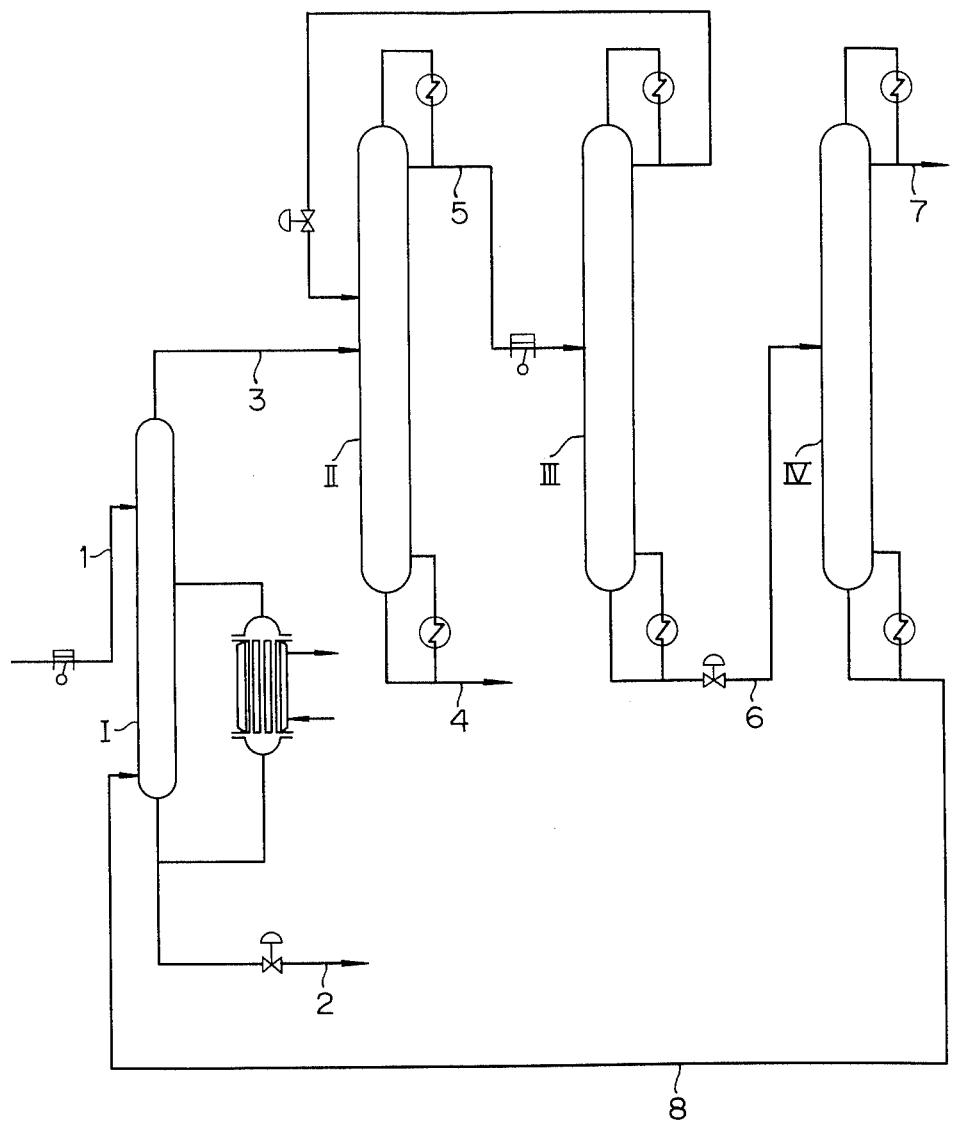

PROCESS FOR PREPARING TETRAHYDROFURAN

BACKGROUND OF THE INVENTION

This inventiion relates to an improved process for producing tetrahydrofuran by the dehydrocyclization of 1,4-butanediol in the presence of an acid catalyst. Tetrahydrofuran is a very useful substance as a solvent for high molecular substances, in particular, polyvinyl chloride, polyvinylidene chloride and it is produced by various processes.

It is known to produce tetrahydrofuran by the dehydrocyclization of 1,4-butanediol in the presence of an acid catalyst as described in British Pat. No. 1,170,222. However such a known process has not achieved sufficient conversion rate and has not been satisfactory from an industrial point of view. Further, since water and tetrahydrofuran, the reaction products, form an azeotropic mixture, it is difficult to recover highly pure tetrahydrofuran in a high yield by conventional distillation.

SUMMARY OF THE INVENTION

One object of this invention is to provide an industrially advantageous process for producing tetrahydrofuran from 1,4-butanediol.

Another object of this invention is to provide a process for producing tetrahydrofuran of high purity in a high yield from crude 1,4-butanediol.

The foregoing objects can easily be attained by taking out, in a gaseous state, the reaction products which obtained by the dehydrocyclization of 1,4-butanediol in the presence of a non-volatile acid catalyst from a reactor and subjecting said reaction products to an azeotropic distillation operation by use of three distillation columns.

BRIEF DESCRIPTION OF THE DRAWING

The drawing is a flow sheet showing one embodiment of this invention.

DETAILED DESCRIPTION OF THE INVENTION

The raw material 1,4-butanediol used in the process of this invention can be prepared in a conventional manner. It is known to prepare 1,4-butanediol by various processes such as hydrogenation of butynediol, or methanolysis of the oxo-reaction product of allyl acetate. It is particularly preferred to use 1,4-butanediol obtained by hydrolizing 1,4-diacetoxybutane which is the hydrogenation product of 1,4-diacetoxybutene prepared by the acetoxylation of butadiene.

1,4-diacetoxybutene is prepared by reacting butadiene, acetic acid, and molecular oxygen in the presence of a palladium-based catalyst and, occasionally, in the presence of a solvent, wherein the acetoxylation is carried out by a known process. 1,4-diacetoxybutene is prepared by reacting butadiene, acetic acid, and oxygen or an oxygen-containing gas in the presence of a palladium-based catalyst in any one of the following methods; for example, fixed-bed, fluidized-bed, and suspensoid process.

Various types of catalysts may be used in the acetoxylation reaction, and preferred catalysts comprise metal palladium in combination with at least one of the metal co-catalysts selected from bismuth, selenium, antimony and tellurium supported on a suitable carrier. The amounts of the catalyst metals carried in a catalyst are usually selected in a concentration of 0.1 to 20 % by weight for the metal palladium and 0.01 to 30 % by weight for the metal co-catalyst. The acetoxylation is carried out at a temperature usually within a range of 40° to 180° C and, preferably, 60° to 150° C under a pressure exceeding atmospheric pressure.

Then, water, acetic acid, high boiling substances and the catalyst are separated from the acetoxylation reaction products to produce diacetoxybutene. The thus obtained diacetoxybutene may be exclusively 1,4-diacetoxybutene-2 or, as the case may be, a mixture thereof with isomers such as 3,4-diacetoxybutene-1.

The diacetoxybutene thus obtained is then subjected to the hydrogenating reaction. The feed hydrogen should not always be pure, and it may be diluted with an inert gas as such nitrogen or with a saturated hydrocarbon such as methane, in which the hydrogen content is not particularly restricted but, preferably, is greater than 10% by volume and, more preferably, greater than 50 % by volume.

The catalysts used for the reaction are the usual hydrogenation catalysts, for example metals such as Pd, Pt, Ni, Ru, Fe, Os, Rh, Ir, Cr, Mo, W and V supported on a carrier.

Active carbon, alumina, silica gel, silica-alumina, clay, bauxite, magnesia, diatomaceous earth, pumice and the like are generally suitable as carriers for the hydrogenation catalysts. Activated carbon is especially preferred.

The hydrogenation reaction is usually carried out at a temperature of 40° to 200° C, preferably, 50° to 100° C and under a pressure of atmospheric pressure to 200 kg/cm$^2$ gauge, preferably, 10 to 100 kg/cm$^2$ gauge.

While the products obtained from the hydrogenation reaction contain, in addition to diacetoxybutane, 1-hydroxy-4-acetoxybutane, high-boiling substances and, as the case may be, 4-acetoxybutyraldehyde, these products can be subjected to hydrolysis without removing the aforementioned substances.

The hydrolysis of the hydrogenation reaction products thus obtained is preferably performed in the presence of a solid acid catalyst. As the solid acid catalyst, cation exchange resins are preferred since they cause the hydrolysis reaction to proceed at a high rate while producing fewer by-products. Specifically, strong acidic cation exchange resins of the sulfonic acid type, the matrix of which consists of styrene-divinylbenzene copolymer, are useful. They may either be so-called gel type resins or porous type resins, as for example, DIAION SK1B, SK103, SK106 (a gel type); PK206, PK216, PK228 (a porous-type); all manufactured by Mitsubishi Chemical Industries Ltd.

The hydrolysis reaction is conducted usually at 30° to 110° C and, preferably 40° to 90° C. The pressure used in the hydrolysis reaction is particularly limited and is selected usually within the range of atmospheric pressure to 10 kg/cm$^2$ gauge.

Water is one of the reactants for the hydrolysis reaction and is also used as a solvent. Therefore, the amount of water used is more than the stoichiometric amount and is usually from 2 to 100 mol, preferably, 4 to 50 mol per mol of diacetoxybutane. The reaction is conducted in various ways and, usually, by applying a stream of diacetoxybutane and water downwardly to a fixed bed filled with the acidic cation exchange resin.

The hydrolyzates are then distilled to produce 1,4-butanediol as a raw material in the present process.

Any method can be applied for distillation so long as it can remove water, acetic acid, unreacted diacetoxybutane, monohydroxy-monoacetate, partially hydrolyzed products, and, as the case may be, 1,2- or 1,3-diols, other than 1,4-butanediol, which are contained in the hydrolyzates. That is to say, crude 1,4-butanediol obtained from the hydrolyzates through distillation thereby to remove those substances having a boiling point lower than that of 1,4-butanediol can be used directly as the raw material for the process according to this invention.

This invention will be explained referring to the accompanying drawing.

In the drawing reference (I) represents a reactor, (II) a first distillation column, (III) a second distillation column and (IV) a third distillation column.

Any type of reactor can be used provided that heating can be effected therein. Especially suitable are those reactors of a thermosyphone reboiler type. The reactor may be made of stainless steel of SUS 316 and 317 but, preferably, of Hastelloy (trade mark of INCO) since the latter has better corrosion resistance. A glass lining gives the best corrosion resistance to the reactor is best fitted for industrial use from the economical point of view.

The non-volatile acid catalysts used in this invention include both liquid and solid acids. Liquid acids including inorganic acids such as sulfuric acid or phosphoric acid and organic acids such as benzenesulfonic acid, paratoluene sulfonic acid, trifluoromethane sulfonic acid or the like are usually used. Sulfuric acid is the most preferred since it is inexpensive and easy to use. The amount of acid required varies depending on the sort of acid and it is difficult to uniformly specify the range therefor. It is usually applied in an amount of 0.1 to 99 parts by weight and, preferably, 5 to 90 parts by weight per 100 parts by weight of the liquid components contained in the reactor. The liquid acids may either be present previously in the reactor or fed continuously to the reactor together with crude 1,4-butanediol as a raw material.

The 1,4-butanediol as a raw material is fed, depending on the case, together with the acid as the catalyst to the reactor (I) through a conduit 1.

The reactor is kept at a temperature capable of maintaining a pressure therein at a sufficient level such that the tetrahydrofuran and water produced in the reactor can move in the vapor phase to the first distillation column due to autogenetic pressure. The reaction temperature is therefore determined in correlation with the operation pressure in the first distillation column and should usually be above 90° C. However, the temperature is preferably less than 220° C and, more preferably, from 110° to 160° C since excessively high temperatures will cause undesirable side reactions.

The reaction pressure should be a little higher than the pressure in the first distillation column and usually be selected within the range of 0 to 3 kg/cm$^2$ gauge.

The mixed vapor effluent from the upper portion of the reactor contains tetrahydrofuran and water in about an equi-molar amount and it is fed through conduit 3 to the first distillation column (II). On the other hand, high boiling substances which have been supplied together with the raw material and produced as by-products in the reaction, spent catalysts and the like are properly discharged from the bottom of the reactor through conduit 2 to the outside of the reaction system.

In the first distillation column, a vapor mixture of tetrahydrofuran and water fed from the reactor and an azeotropic mixture of tetrahydrofuran and water recycled from the second distillation column are supplied to be distilled. The first distillation column is operated with 5 to 30 number of theoretical plates, under a pressure of from atmospheric pressure to 3 kg/cm$^2$ gauge and with a reflux ratio of 0.5 to 5, preferably, 1 to 3. An azeotropic mixture of tetrahydrofuran and water (THF : H$_2$O = 81 : 19 – 74 : 26, in molar ratio) is distilled from the top of the column and supplied through conduit 5 to the second distillation column, and water is removed from the bottom of the column through conduit 4. The effluent from the top of the first distillation column is pressured by means of pump and supplied to the second distillation column (III). The second distillation column is operated with 5 to 30 number of theoretical plates, maintained under a pressure higher than the first distillation column by 3 to 20, preferably, 5 to 15 kg/cm$^2$ gauge, that is at a pressure of from 3 to 23, preferably, 5 to 18 kg/cm$^2$ gauge and with a reflux ratio of 0.5 to 5, preferably, 1 to 3. An azeotropic mixture of tetrahydrofuran and water (THF : H$_2$O = 74 : 26 – 53 : 47, preferably, 69 : 31 – 55 : 45) is distilled from the top of the second distillation column and circulated to the first distillation column and, while on the other hand, tetrahydrofuran substantially free from water is obtained from the bottom of the second distillation column.

While the tetrahydrofuran thus produced has a considerably high purity and can be used as a commercial product as is, it can further be purified if required. For instance, the bottom discharged from the second distillation column can be supplied through conduit 6 to a third distillation column (IV) to produce tetrahydrofuran of higher purity through conduit 7. The third distillation column is usually operated with 10 to 30 number of theoretical plates, under a atmospheric pressure or a pressure slightly higher than atmospheric pressure and with a reflux ratio of 0.5 to 2.0.

If the bottom discharged from the third distillation column is recycled through conduit 8 to the dehydrocyclization system, additional industrial advantages can be obtained. That is, in the dehydrocyclization, system n-butyraldehyde is inevitably produced as a by-product and cannot be easily separated completely by distillation from tetrahydrofuran. On the other hand, since n-butyraldehyde is unstable in the presence of the acidic catalyst and changes into higher boiling substances and the like, the concentration of n-butyraldehyde in the dehydrocyclization reaction system does not exceed a certain level which depends on the reaction conditions. Therefore, by recycling the bottom discharged from the third distillation column having a high-n-butyraldehyde content to the reaction system, the amount of n-butyraldehyde in the reaction products can be kept below a certain value thereby preventing a decrease in the tetrahydrofuran yield and improving the purity thereof.

As described above, according to the process of this invention, tetrahydrofuran of very high quality can be obtained from the bottom of a distillation column by taking out the reaction products in a gaseous state from the reactor and subjecting them directly to the distillation wherein the distillation is carried out in three distillation columns under specified conditions.

Moreover, since the reaction products are transferred in their gaseous state, the present reaction can be performed with no difficulty even when substances having a boiling point similar to or higher than the boiling point of 1,4-butanediol are present in the 1,4-butanediol. Therefore, the present invention is economically advantageous.

The process according to this invention will be further described by way of the following example. This example is for illustrative purposes only and is not meant to limit or in anyway redefine the invention as claimed in the generic claim of the present application.

Diacetoxybutene which had been prepared by catalytically reacting butadiene, acetic acid and an oxygen-containing gas with a palladium-based catalyst at 80° to 100° C, was hydrogenated in the presence of a palladium catalyst carried on activated carbon to produce diacetoxybutane having the composition set forth below. The resulting diacetoxybutane was then hydrolyzed in the presence of a cation exchange resin, DIAION SK1B, (trade mark, manufactured by Mitsubishi Chemical Industries Ltd.) at about 60° C and subjected to distillation to prepare crude 1,4-butanediol, which contained 98.5 % by weight of 1,4-butanediol, 0.7 % by weight of high boiling substances and 0.8 % by weight of other substances.

Composition for Diacetoxybutane 1,4-diacetoxybutane: 86.3 % by weight
1-hydroxy-4-acetoxybutane: 4.4 % by weight
Acetoxybutyraldehyde: 0.2 % by weight
Butylacetate: 1.7 % by weight
High boiling substances: 0.4 % by weight 10.0 kg of crude 1,4-butanediol thus prepared was mixed with 10 g of $H_2SO_4$ and fed to reactor (I) at a rate of 0.64 kg/hr. The reactor is made of a Hastelloy (trade mark of INCO), 50 mm in inner diameter and 1 m in length and provided with a steam heating type reboiler containing three pipes each 10 mm in outer diameter and 8 mm in inner diameter. The steam supplied to the reboiler was conditioned to maintain the inside temperature of the reactor at 130° C. A mixture of tetrahydrofuran and water in a 1 : 1 molar ratio was discharged in the vapor phase from the top of the reactor at a rate of 0.63 kg/hr. The mixed vapor was fed by autogenetic pressure to the first distillation column (II) (50 mm in inner diameter and 10 m in height, filled with Dickson packings). The distillation column was operated under atmospheric pressure with a reflux ratio of 2.0 to obtain a liquid distillate comprising 94.4 % by weight of tetrahydrofuran, 5.6 % by weight of water and 190 ppm by weight of n-butyraldehyde at 0.893 kg/hr from the top thereof. The distillate was then sent by way of a pump to a second distillation column (150 mm in inner diameter and 10 m in height, filled with Dickson packings), distilled under a pressure of 7 kg/cm² gauge with a reflux ratio of 4.0. The liquid distillate comprising 87.2 % by weight of tetrahydrofuran and 12.8 % by weight of water was discharged from the top of the column at a rate of 0.391 kg/hr and then recycled to the first distillation column. While on the other hand, tetrahydrofuran with more than 99.95 wt% of purity was obtained as the bottom at a rate of 0.502 kg/hr from the bottom of the second distillation column. The bottom contained 200 ppm of n-butyraldehyde.

The bottom discharged from the second distillation column at the rate of 0.502 kg/hr was then supplied by means of a pump to a third distillation column (IV) (150 mm in inner diameter, 10 m in height and filled with Dickson packings), which was operated under atmospheric pressure with a reflux ratio of 2.0 to obtain tetrahydrofuran with 99.97 wt% of purity as liquid distillate at a rate of 0.477 kg/hr from the top of thereof. The n-butyraldehyde content in the distillate was 130 ppm by weight. The bottom containing 1500 ppm by weight of n-butyraldehyde was produced at a rate of 0.025 kg/hr from the bottom of the column (IV). When the overall operation was carried out by recycling the above-described bottom to the reaction zone, the butyraldehyde content in the distillate from the third distillation column was reduced to 120 to 140 ppm by weight.

What is claimed is:

1. A process for preparing tetrahydrofuran by the dehydrocyclization reaction of 1,4-butanediol in the presence of an acid catalyst, consisting essentially of;
   (a) supplying 1,4-butanediol and a non-volatile acid catalyst to a reaction zone,
   (b) reacting said butanediol and said catalyst at a temperature between above the boiling point of an azeotropic mixture of water and tetrahydrofuran and below the boiling point of 1,4-butanediol,
   (c) continuously removing a vapor mixture of water and tetrahydrofuran from said reaction zone,
   (d) supplying said vapor mixtures to a first distillation column maintained under a pressure lower than that in said reaction zone and in the range of from atmospheric pressure to 3 kg/cm² gauge,
   (e) distilling a first azeotropic mixture of water and tetrahydrofuran to form a first distillate,
   (f) supplying said first distillate to a second distillation column maintained under a pressure higher than that in said first distillation column by 3 to 20 kg/cm² gauge,
   (g) distilling a second azeotropic mixture of water and tetrahydrofuran from the top of said second distillation column to form a second distillate,
   (h) recycling said second distillate to said first distillation column,
   (i) supplying a substantially water-free-bottom of said second distillation column to a third distillation column maintained under atmospheric pressure or a pressure slightly higher than atmospheric pressure,
   (j) recycling the bottom of said third distillation column into said reaction zone, and
   (k) obtaining tetrahydrofuran from the top of said third distillation column.

2. The process for preparing tetrahydrofuran according to claim 1, wherein 1,4-butanediol is prepared by hydrogenating 1,4-diacetoxybutene, which is produced by the acetoxylation of butadiene, into 1,4-diacetoxybutane and hydrolyzing said 1,4-diacetoxybutane as the hydrogenated products in the presence of a solid acid catalyst and distilling hydrolyzates thus obtained.

3. The process for preparing tetrahydrofuran according to claim 1, wherein the non-volatile acid catalyst is a liquid acid catalyst.

4. The process for preparing tetrahydrofuran according to claim 3, wherein the non-volatile liquid acid is sulfuric acid.

5. The process for preparing tetrahydrofuran according to claim 4, wherein sulfuric acid is fed continuously to the reactor together with crude 1,4-butanediol.

6. The process for preparing tetrahydrofuran according to claim 1, wherein the reaction temperature is in the range of 90° to 220° C.

7. The process for preparing tetrahydrofuran according to claim 1, wherein the first and second distillation columns are operated with 5 to 30 number of theoretical plates.

8. The process for preparing tetrahydrofuran according to claim 1, wherein the third distillation column is operated with 10 to 30 number of theoretical plates.

9. The process for preparing tetrahydrofuran according to claim 1, wherein the first and second distillation columns are operated with a reflux ratio of 0.5 to 5.

10. The process for preparing tetrahydrofuran according to claim 1, wherein the third distillation column is operated with a reflux ratio of 0.5 to 2.0.

* * * * *